US00PP26958P2

(12) United States Plant Patent
Li

(10) Patent No.: US PP26,958 P2
(45) Date of Patent: Jul. 19, 2016

(54) ***VERBENA* PLANT NAMED 'KLEVP15498'**

(50) Latin Name: ***Verbena* sp.**
Varietal Denomination: KLEVP15498

(71) Applicant: Klemm+Sohn GmbH & Co. KG, Stuttgart (DE)

(72) Inventor: Ruijun Li, North Parramata (AU)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,039

(22) Filed: Mar. 19, 2015

(51) Int. Cl.
*A01H 5/02* (2006.01)

(52) U.S. Cl.
USPC ..... Plt./308

(58) Field of Classification Search
USPC ..... Plt./308
CPC ..... A01H 5/02
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

A new *Verbena* plant particularly distinguished by dark blue-violet flowers with white eyes, early flowering, and good resistance to powdery mildew, is disclosed.

1 Drawing Sheet

Genus and species: *Verbena* sp.
Variety denomination: 'KLEVP15498'.

BACKGROUND OF THE NEW PLANT

The present invention comprises a new and distinct variety of *Verbena*, botanically known as *Verbena* sp., and hereinafter referred to by the variety name 'KLEVP15498'. 'KLEVP15498' originated from a cross-pollination conducted in September 2010 in Cobbitty, New South Wales, Australia between the proprietary female *Verbena* variety 'VC11ABV' (unpatented), and the proprietary male *Verbena* variety 'VC11 0126' (unpatented).

The seeds from the cross were sown and plants were grown for evaluation, where an individual plant designated 'KLEVP15498' was selected from the group of plants in Cobbitty, New South Wales, Australia in April 2011.

In April 2011, 'KLEVP15498' was first vegetatively propagated by vegetative cuttings in Cobbitty, NSW, Australia. 'KLEVP15498' was found to reproduce true to type in successive generations of asexual propagation via vegetative cuttings.

SUMMARY

The following are the most outstanding and distinguishing characteristics of this new variety when grown under normal horticultural practices in Cobbitty, New South Wales, Australia.

1. Dark blue-violet flowers with white eyes;
2. Early flowering; and
3. Good resistance to powdery mildew.

DESCRIPTION OF THE PHOTOGRAPH

This new *Verbena* plant is illustrated by the accompanying photograph which shows the plant's overall plant habit including form, foliage, and flowers. The photograph is of a three-month old plant grown in a greenhouse in Stuttgart, Germany in May 2013. The colors shown are as true as can be reasonably obtained by conventional photographic procedures.

DESCRIPTION OF THE NEW VARIETY

The following detailed descriptions set forth the distinctive characteristics of 'KLEVP15498'. The data which define these characteristics were collected from asexual reproductions carried out in Cobbitty, New South Wales, Australia. Data was collected on three-month-old plants grown in a greenhouse in Cobbitty, New South Wales, Australia in February 2015 in Cobbitty, New South Wales, Australia. Color references are to The R.H.S. Colour Chart of The Royal Horticultural Society of London (R.H.S.) 2005.

Classification:
- *Family*.—Verbenaceae.
- *Botanical*.—*Verbena* sp.
- *Common*.—*Verbena*.
- *Designation*.—'KLEVP15498'.

Parentage:
- *Female parent*.—The proprietary female *verbena* variety 'VC11ABV' (unpatented).
- *Male parent*.—The proprietary male *verbena* variety 'VC11 0126' (unpatented).

Plant:
- *Growth and branching habit*.—Semi-upright.
- *Height (from top of soil)*.—30.0 cm.
- *Width (horizontal plant diameter)*.—30.0 cm.
- *Time to produce a finished flowering plant*.—Approximately 8 weeks.
- *Time to initiate and develop roots*.—3 weeks.
- *Root description*.—White.

Stems:
- *Number of branches per plant*.—More than 25.
- *Growth habit*.—Semi-upright.
- *Length*.—20.0 cm.
- *Diameter*.—1.0 cm.
- *Internode length*.—Approximately 2.0 cm.
- *Color*.—RHS 130D.

*Anthocyanin*.—Absent.
*Texture and appearance*.—Pubescence, round.

Leaves:
*Arrangement*.—Opposite.
*Immature and mature leaf color*.—Upper surface: RHS 141A. Lower surface: RHS 141C.
*Length*.—2.5 cm.
*Width*.—1.5 cm.
*Shape*.—Lanceolate.
*Apex*.—Acute.
*Base*.—Obtuse.
*Margin*.—Crenate.
*Texture*.—Upper surface: Leathery. Lower surface: Rugose.
*Venation type*.—Pinnate.
*Venation color* (*both upper and lower surfaces*).—RHS 141D.
*Petioles*.—Length: 0.4 cm. Diameter: 0.1 cm. Color: RHS 141D. Texture: Leathery.

Flower buds:
*Shape*.—Tall, cylindrical.
*Length*.—0.5 cm.
*Diameter*.—0.1 cm.
*Color* (*at tight bud*).—RHS 93A.

Inflorescence:
*Blooming habit* (*flowering season*).—Continuously.
*Lastingness of individual blooms on the plant*.—2 weeks.
*Fragrance*.—Absent.
*Inflorescence type*.—Umbel.
*Length of inflorescence*.—6.0 cm.
*Diameter of inflorescence*.—6.0 cm.
*Number of florets per inflorescence*.—More than 15.
*Peduncle*.—Color: RHS 141A. Length: 1.0 cm. Diameter: 0.1 cm.

Florets:
*Length*.—2.0 cm.
*Diameter*.—4.0 cm.
*Texture*.—Glossy.
*Form*.—Single.
*Length*.—1.0 cm.
*Diameter*.—3.0 cm.
*Color*.—Immature: Upper surface: RHS 89A. Lower surface: RHS 94B. Mature: Upper surface: RHS 93B. Lower surface: RHS 94C.
*Corolla tube length*.—1.2 cm.
*Corolla tube color*.—RHS 56C.
*Petals*.—Length of lobe: 2.0 cm. Diameter of lobe: 2.0 cm. Lobe shape: Round. Apex: Acute. Base: Obtuse. Margin: Entire. Texture (both upper and lower surfaces): Glossy, satiny.
*Pedicels*.—Not visible.

Sepals:
*Shape*.—Lanceolate.
*Apex*.—Acute.
*Base*.—Obtuse.
*Margin*.—Entire.
*Length*.—2.0 cm.
*Diameter*.—0.5 cm.
*Color*.—RHS 141C.
*Texture* (*both upper and lower surfaces*).—Hairy, dull.

Reproductive organs:
*Stamens*.—Present. Quantity: 4. Color: RHS 139D. Filament length: 0.6 cm. Filament diameter: Less than 0.1 cm. Anther: Shape: Elliptic. Color: RHS 141D. Length: 0.8 cm. Diameter: 0.2 cm. Pollen amount: Sparse.
*Pistils*.—Number: 1. Length: 1.0 cm. Diameter: 0.1 cm. Stigma: Color: RHS 141D. Appearance: Ovate. Length: 0.1 cm. Diameter: 0.1 cm. Style: Color: RHS 141D. Length: 0.9 cm. Diameter: 0.1 cm. Appearance: Long.

Fruit and seed set: None observed.

Disease and pest/insect resistance: Good resistance to powdery mildew.

COMPARISON WITH PARENTAL LINES AND KNOWN VARIETY

'KLEVP15498' is distinguished from its parents as described in Table 1.

TABLE 1

Comparison with Parental Lines

| Characteristic | Variety 'KLEVP15498' | Female parent 'VC11ABV' | Male parent 'VC11 0126' |
|---|---|---|---|
| Flower color | Dark blue-violet with eyes | Violet | Purple |
| Earliness to flower | Early | Medium | Medium |

'KLEVP15498' is most similar to the commercial *verbena* Empress Imperial Blue (patent status unknown). Differences between the varieties are described in Table 2.

TABLE 2

Comparison with Similar Variety

| Characteristic | Variety 'KLEVP15498' | Commercial line Empress Imperial Line |
|---|---|---|
| Flower color | Dark blue-violet with eyes | Solid purple |
| Resistance to powdery mildew | Good resistance | Less resistance than 'KLEVP15498' |

I claim:

1. A new and distinct variety of *Verbena* plant designated 'KLEVP15498' as illustrated and described herein.

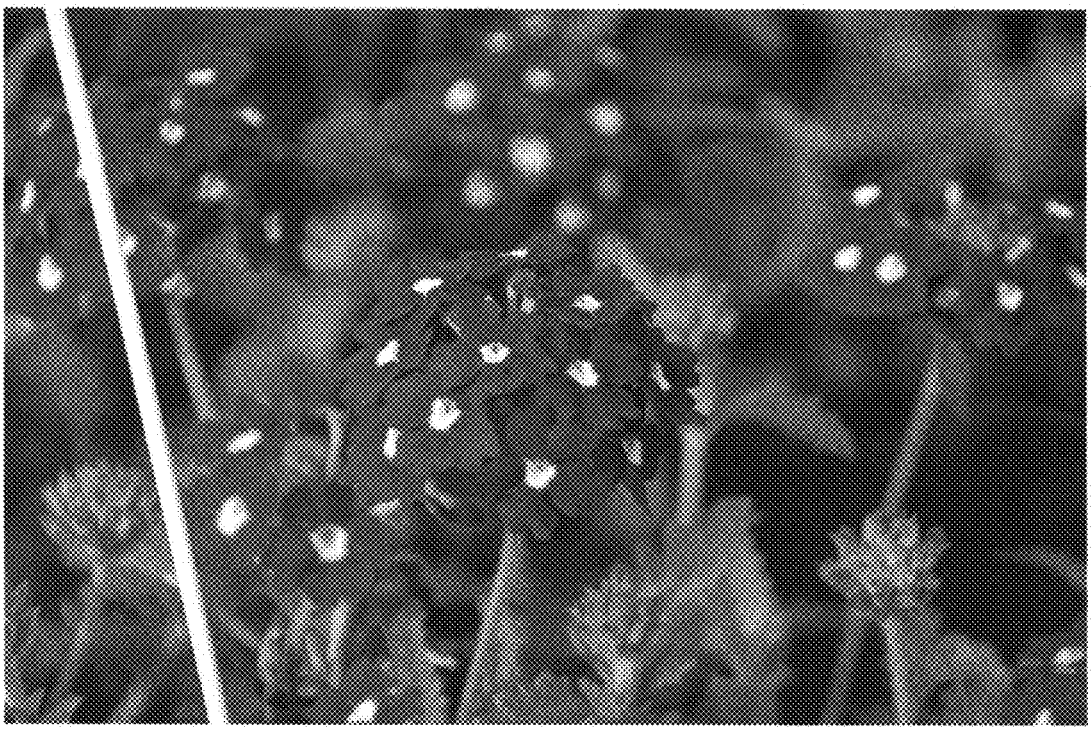

* * * * *